(12) United States Patent
Angermann et al.

(10) Patent No.: US 8,716,184 B2
(45) Date of Patent: May 6, 2014

(54) HERBICIDAL COMPOSITION COMPRISING THE HYDRATES OF SAFLUFENACIL AND GLYPHOSATE OR GLUFOSINATE

(75) Inventors: Alfred Angermann, Kriftel (DE); Stefan Lehr, Liederbach (DE); Hubert Menne, Mainz-Kastel (DE); Lothar Willms, Hofheim (DE); Erwin Hacker, Hochheim (DE); Britta Olenik, Bottrop (DE)

(73) Assignee: Bayer Cropscience AG, Monheim (DE)

( * ) Notice: Subject to any disclaimer, the term of this patent is extended or adjusted under 35 U.S.C. 154(b) by 133 days.

(21) Appl. No.: 13/034,631

(22) Filed: Feb. 24, 2011

(65) Prior Publication Data

US 2011/0212837 A1    Sep. 1, 2011

(30) Foreign Application Priority Data

Feb. 26, 2010    (EP) .................................... 10001998

(51) Int. Cl.
| | |
|---|---|
| *A01N 57/00* | (2006.01) |
| *A01N 57/18* | (2006.01) |
| *A01N 47/36* | (2006.01) |
| *A01N 43/54* | (2006.01) |
| *A01N 57/10* | (2006.01) |
| *A01N 25/26* | (2006.01) |

(52) U.S. Cl.
USPC ........... 504/128; 504/118; 504/203; 504/206; 504/211; 504/214; 504/100; 514/109; 514/274

(58) Field of Classification Search
USPC ......... 504/128, 118, 203, 206, 211, 214, 100; 514/109, 274
See application file for complete search history.

(56) References Cited

U.S. PATENT DOCUMENTS

| | | | |
|---|---|---|---|
| 7,232,926 B2 | 6/2007 | Hamprecht et al. | |
| 7,375,058 B2 | 5/2008 | Zagar et al. | |
| 7,737,275 B2 | 6/2010 | Hamprecht et al. | |
| 2005/0159622 A1 | 7/2005 | Hamprecht et al. | |
| 2009/0042727 A1 | 2/2009 | Evans et al. | |
| 2010/0035905 A1 | 2/2010 | Schmidt et al. | |

FOREIGN PATENT DOCUMENTS

| | | |
|---|---|---|
| DE | 60218707 T2 | 6/2007 |
| WO | 99/13723 | 3/1999 |
| WO | 0183459 | 11/2001 |
| WO | WO 03024221 A1 * | 3/2003 |
| WO | 03097589 | 11/2003 |
| WO | 2005054208 | 6/2005 |
| WO | 2006097509 | 9/2006 |
| WO | 2008043836 | 4/2008 |
| WO | 2009141367 | 11/2009 |
| WO | 2009156322 | 12/2009 |

OTHER PUBLICATIONS

International Search Report Based on PCT/EP2011/052558 Mailed Sep. 14, 2011.

* cited by examiner

*Primary Examiner* — John Pak
*Assistant Examiner* — Andriae M Holt
(74) *Attorney, Agent, or Firm* — Miles & Stockbridge P.C.

(57) ABSTRACT

A herbicide combination comprising a) at least one herbicide (A) selected from the group consisting of glyphosate (A1) and its agrochemically compatible salts, and glufosinate (A2) and its agrochemically compatible salts, and b) a herbicide (B) which is a hydrate of the compound 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide, and the use thereof for controlling harmful plants.

13 Claims, No Drawings

HERBICIDAL COMPOSITION COMPRISING THE HYDRATES OF SAFLUFENACIL AND GLYPHOSATE OR GLUFOSINATE

CROSS REFERENCE TO RELATED APPLICATIONS

This application claims priority to EP10001998.3 filed Feb. 26, 2010, the content of which is incorporated herein by reference in its entirety.

BACKGROUND OF THE INVENTION

Field of the Invention

The present invention relates to a herbicide combination comprising
a) at least one herbicide (A) selected from the group consisting of
  glyphosate (A1) and its agrochemically compatible salts, and
  glufosinate (A2) and its agrochemically compatible salts, and
b) a herbicide (B) which is a hydrate of the compound 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide.

2. Description of Related Art

The phenyluracil of the formula (I)

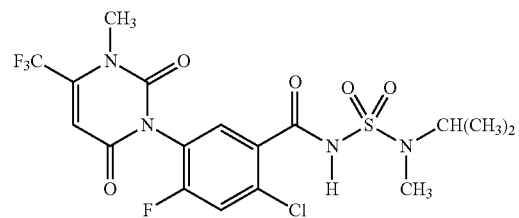

(I)

corresponding to component (B) is a compound having herbicidal properties. This active component, which is already known from document WO 01/083459, is known under the common name saflufenacil.

Processes for preparing the phenyluracil of the formula (I) in the form of an amorphous substance are known from WO 01/083459, WO 03/097589, WO 05/054208 and WO 06/097509.

Because of stability problems, however, the amorphous phenyluracil of the formula (I) has been found to be of only limited suitability for producing formulations. Stability problems occur, according to WO 2008/043836, when the compound of the formula (I), in its amorphous state, is used, in particular, in multiphase formulations.

With regard to the aforementioned difficulties, WO 2008/043836, discloses how the hydrates of the phenyluracil of the formula (I) do not have the stability problems of the amorphous form, and how the hydrates, moreover, exhibit better herbicidal activity and also better selectivity in a range of crops.

With regard to the characterization of the hydrates of the phenyluracil of the formula (I) as disclosed in WO 2008/043836, by means of chemical and physical methods, WO 2008/043836 is incorporated here in full by reference.

The hydrates of the phenyluracil of the formula (I) are crystalline substances which are crystallized in a more compact form than the amorphous forms of the phenyluracil of the formula (I) that are known from WO 01/083459.

The hydrates of the phenyluracil of the formula (I) are crystalline substances which, depending on the formation of the crystals, contain about 0.8 to 1.2 mol of water, more particularly 0.9 to 1.1 mol, and especially 0.95 to 1.05 mol/mol of phenyluracil, and are therefore considered to be monohydrates.

For the preparation of the hydrates of the phenyluracil of the formula (I), crystallization from a solution of the phenyluracil of the formula (I) in an organic solvent in the presence of water proved to be a central step.

With regard to the preparation of the hydrates of the compound according to formula (I), the disclosure content of WO 2008/043836 is hereby incorporated in full by reference.

Additionally known from the prior art (WO 2009/141367) are compositions with herbicidal action which in addition to glyphosate and glufosinate or salts thereof comprise at least two other active herbicidal compounds, one of the active compounds being pyroxasulfone. As a third active combination compound, WO 2009/141367 also discloses the use of the phenyluracil of the formula (I) (saflufenacil) (see the saflufenacil examples 260 to 321, especially example 273).

WO 2009/156322 relates to a further herbicide combination which can comprise the phenyluracil, including saflufenacil, in combination with glyphosate, the purpose of the phenyluracil component being to improve the rain resistance of the glyphosate component.

The use of the hydrates of the phenyluracil of the formula (I) as components in a combination product has not hitherto been disclosed.

SUMMARY OF THE INVENTION

The object of the present invention lies in the provision of further compositions with herbicidal effect which comprise one or more hydrates of the phenyluracil of the formula (I) and have advantages over the compositions known from the prior art.

The object is achieved by means of a herbicide combination comprising
a) at least one herbicide (A) selected from the group consisting of
  glyphosate (A1) and its agrochemically compatible salts, and
  glufosinate (A2) and its agrochemically compatible salts, and
b) a herbicide (B) which is a hydrate of the compound 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide.

DETAILED DESCRIPTION OF A PREFERRED EMBODIMENT

Glyphosate (the common name of the compound having the IUPAC name N-(phoshonomethyl)glycine) is a nonselective herbicide, described in U.S. Pat. No. 3,799,758 and U.S. Pat. No. 4,405,531. Glyphosate is known under the trade names Roundup™ and Touchdown™.

Glyphosate is also provided as a salt with various cations. Examples of glyphosate salts used as herbicides are glyphosate-diammonium [CAS RN 69254-40-6] (A1a), glyphosate-isopropylammonium [38641-94-0] (A1b), glyphosate-monoammonium [40465-66-5] (A1c), glyphosate-potassium

[70901-20-1] (A1d), glyphosate-sesquisodium [70393-85-0] (A1e), and in the form of glyphosate-trimesium [81591-81-3] (A1f).

Glyphosate employed as component (A1) in the present invention is used preferably in the diammonium (A1a), isopropylammonium (A1b), monoammonium (A1c) or trimesium salt (A1f) form.

Further specific forms for use of glyphosate are the formulations protected by trade names given below: Roundup Original™, Roundup Transarb™, and Roundup WG™.

Glufosinate (the common name of the compound having the IUPAC name 4[hydroxy(methyl)phosphinoyl]-DL-homoalanine) [CAS RN 53369-07-6] is another nonselective herbicide. The racemic mixture of the herbicidal active compound is distinguished from the L-isomer [CAS RN 35597-44-5], which is likewise noted for herbicidal action.

Glufosinate and its salts, such as glufosinate-ammonium [CAS RN 77 182-82-2], for example, and its herbicidal effect have been described by F. Schwerdtle et al., Z. Pflanzenkr. Pflanzenschutz, 1981, special edition IX, pp. 431-440.

For the present invention where glufosinate is used as component (A2), particularly interesting glufosinate salts are glufosinate-ammonium (A2a), glufosinate-sodium (A2b), L-glufosinate-ammonium (A2c), and L-glufosinate-sodium (A2d).

The most preferred is glufosinate-ammonium (A2a).

Glufosinate and its salts are known under the trade names such as Basta™, Liberty™, Ignite™, Rely™, and Finale™, for example.

In one preferred embodiment of the herbicide combination, for component (B) in the state prior to the mixing of component (B) with the other components and constituents of the herbicide combination, it is the case that the hydrates of the compound 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide contain 0.8 to 1.2 mol of water per mole of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide.

The aforementioned hydrates of component (B) have a melting point in the range from 100 to 140° C.

The aforementioned hydrates of component (B) are additionally notable for the fact that component (B), in the state prior to the mixing of component (B) with the other components and constituents of the herbicide combination, has a 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide content of at least 94% by weight, based on the total amount of the organic constituents present in the hydrate.

In one particularly preferred embodiment of the herbicide combination, the component (B), in the state prior to the mixing of component (B) with the further components and constituents of the herbicide combination, in an X-ray powder diffractogram at 25° C. with Cu-Kα radiation, shows at least one reflection at the 2θ value 11.6±0.2°. If component (B) is present in this particular crystal form, it is identified (in delimitation from other possible crystal forms of component (B)) as component (Ba).

In one especially preferred embodiment of the herbicide combination, component (Ba), in the state prior to the mixing of component (Ba) with the further components and constituents of the herbicide combination, in an X-ray powder diffractogram additionally shows at least three of the following reflections reported as 2θ values: 5.1±0.2°, 10.1±0.2°, 10.8±0.2°, 13.9±0.2°, 15.1±0.2°, 16.1±0.2°, 17.9±0.2°, 20.2±0.2°, 24.5±0.2°.

In another particularly preferred embodiment of the herbicide combination, component (B), in the state prior to the mixing of component (B) with the further components and constituents of the herbicide combination, in an X-ray powder diffractogram at 25° C. with Cu-Kα radiation, shows at least one reflection at the 2θ value 12.1±0.2° C. This particular crystal form of component (B) is referred to (in delimitation from other possible crystal forms of component (B)) as component (Bb).

In one especially preferred embodiment of the herbicide combination, component (Bb), in the state prior to the mixing of component (Bb) with the further components and constituents of the herbicide combination, in an X-ray powder diffractogram shows at least three of the following reflections reported as 2θ values: 5.2±0.2°, 10.2±0.2°, 10.9±0.2°, 14.0±0.2°, 14.6±0.2°, 15.3±0.2°, 19.2±0.2°, 19.9±0.2°, 20.5±0.2°, 24.7±0.2°, 26.7±0.2°, 27.8±0.2°.

Preferred proportions of components (A):(B) for the combinations according to the invention are set out below:

The weight ratio of the components (A) to the components (B) in the herbicide combination may lie in each case in the range between 1600:1 to 1:10.

Particular preference is given to the weight ratio of component (A) to component (B) in the range between 800:1 to 1:5.

In the combinations according to the invention, the application rates can as a rule be reduced in comparison to the application rates for the individual compounds.

In one preferred embodiment, herbicide combinations according to the invention comprise, as additional component (C), one or more components selected from the group consisting of active agrochemical compounds of other kinds, and also customary crop protection additives, and formulating assistants.

In addition to herbicides, fungicides, insecticides, acaricides, nematicides miticides, and related compounds, active agrochemical compounds of other kinds include, in particular, herbicides which are nonidentical with the active compounds of components (A) and (B). Furthermore, active agrochemical compounds of other kinds also include compounds which act as active crop plant protectant compounds (called "safeners" or "antidotes"), or growth regulators.

Compounds used with preference as further herbicides (C), which differ structurally from the herbicides (A) and (B), and hence are not identical with them, include active herbicidal compounds which are based on inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase, as described in, for example, Weed Research 26, 441-445 (1986), or "The Pesticide Manual", 13th edition, The British Crop Protection Council, 2003, or 14th edition 2006/2007, or in the corresponding "e-Pesticide Manual", Version 4 (2006), in each case published by the British Crop Protection Council (and also referred to for short below as "PM"), and literature cited therein.

Lists of common names are also available on the Internet in "The Compendium of Pesticide Common Names". The herbicides are identified either by their common name according to the International Organization for Standardization (ISO) or by the chemical names, where appropriate together with a standard code number, and in each case encompass all of the application forms, such as acids, salts, esters, and isomers, such as stereoisomers and optical isomers.

One application form and in some cases two or more application forms as well are identified, with the following compounds all being suitable as component (C) in the present invention:

acetochlor; acibenzolar-S-methyl; acifluorfen(-sodium); aclonifen; AD-67; AKH 7088, i.e., [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; aminocyclopyrachlor; aminopyralid; amitrol; ammonium pelargonate; AMS, i.e., ammonium sulfamate; ancimidol; asulam; atrazine; aviglycine; azafenidin, azimsulfuron (DPX-A8947); aziprotryn; barban; BAS 516 H, i.e., 5-fluoro-2-phenyl-4H-3,1-benzoxazin-4-one; beflubutamid (UBH-509), benazolin(-ethyl); bencarbazone; benfluralin; benfuresate; bensulfuron(-methyl); bentazone; benzfendizone; benzobicyclon, benzofenap; benzofluor; benzoylprop(-ethyl); benzthiazuron; bicyclopyrone; bifenox; bispyribac(-sodium) (KIN-2023); borax; bromacil; bromobutide; bromofenoxim; bromoxynil; bromuron; buminafos; busoxinone; butachlor; butafenacil; butenachlor (KH-218); buthidazole; butralin; butroxydim; butylate; cafenstrole (CH-900); caloxydim; carbetamide; carfentrazone(-ethyl); catechin; CDAA, i.e., 2-chloro-N,N-di-2-propenylacetamide; CDEC, i.e., 2-chlorallyl diethyldithiocarbamate; chlormesulon; chlomethoxyfen; chloramben; chlorazifop-butyl; chlorbromuron; chlorbufam; chlorfenac; chlorfenprop; chlorflurecol(-methyl); chlorflurenol(-methyl); chloridazon; chlorimuron(-ethyl); chlormequat(-chloride); chlornitrofen; chlorophthalim (MK-616); chlorotoluron; chloroxuron; chlorpropham; chlorsulfuron; chlorthal-dimethyl; chlorthiamid; chlortoluron; cinidon(-methyl and -ethyl); cinmethylin; cinosulfuron; clefoxydim; clethodim; clodinafop and its ester derivatives (e.g., clodinafop-propargyl); clofencet; clomazone; clomeprop; cloprop; cloproxydim; clopyralid; clopyrasulfuron(-methyl); cloransulam(-methyl); cumyluron (JC 940); cyanamide; cyanazine; cycloate; cyclosulfamuron (AC 104); cycloxydim; cycluron; cyhalofop and its ester derivatives (e.g., butyl ester, DEH-112); cyperquat; cyprazine; cyprazole; daimuron; 2,4-D; 2,4-DB; dalapon; daminozide; dazomet; n-decanol; desmedipham; desmetryn; di-allate; dicamba; dichlobenil; dichlormid; dichlorprop(-P) salts; diclofop and its esters such as diclofop-methyl; diclofop-P(-methyl); diclosulam; diethatyl(-ethyl); difenoxuron; difenzoquat(-metilsulfate); diflufenican; diflufenzopyr(-sodium); dimefuron; dimepiperate; dimethachlor; dimethametryn; dimethazone; dimethenamid (SAN-582H); dimethenamid-P; dimethylarsinic acid; dimethipin; dimetrasulfuron; dimexyflam; dinitramine; dinoseb; dinoterb; diphenamid; dipropetryn; diquat salts; dithiopyr; diuron; DNOC; eglinazine-ethyl; EL 77, i.e., 5-cyano-1-(1,1-dimethylethyl)-N-methyl-1H-pyrazole-4-carboxamide; endothal; epoprodan; EPTC; esprocarb; ethalfluralin; ethametsulfuron-methyl; ethidimuron; ethiozin; ethofumesate; ethoxyfen and its esters (e.g., ethyl ester, HN-252); ethoxysulfuron; etobenzanid (HW 52); F5231, i.e., N-[2-chloro-4-fluoro-5-[4-(3-fluoropropyl)-4,5-dihydro-5-oxo-1H-tetrazol-1-yl]phenyl]ethanesulfonamide; fenchlorazole(-ethyl); fenclorim; fenoprop; fenoxan, fenoxapropand fenoxaprop-P and also their esters, e.g., fenoxaprop-P-ethyl and fenoxaprop-ethyl; fenoxydim; fentrazamide; fenuron; ferrous sulfate; flamprop(-methyl or -isopropyl or -isopropyl-L); flamprop-M(-methyl or -isopropyl); flazasulfuron; floazulate (JV-485); florasulam; fluazifop and fluazifop-P and the esters thereof, e.g., fluazifop-butyl and fluazifop-P-butyl; fluazolate; flucarbazone(-sodium); flucetosulfuron; fluchloralin; flufenacet; flufenpyr(-ethyl); flumetralin; flumetsulam; flumeturon; flumiclorac(-pentyl); flumioxazin (S-482); flumipropyn; fluometuron; fluorochloridone; fluorodifen; fluoroglycofen(-ethyl); flupoxam (KNW-739); flupropacil (UBIC-4243); flupropanoate; flupyrsulfuron(-methyl)(-sodium); flurenol(-butyl); fluridone; fluorochloridone; fluoroxypyr(-meptyl); flurprimidol; flurtamone; fluthiacet(-methyl) (KIN-9201); fluthiamide; fluxofenim; fomesafen; foramsulfuron; forchlorfenuron; furyloxyfen; gibberillic acid; halosafen; halosulfuron(-methyl); haloxyfop and its esters; haloxyfop-P (=R-haloxyfop) and its esters; HC-252; hexazinone; HNPC-C9908, i.e., methyl 2-[[[[[4-methoxy-6-(methylthio)-2-pyrimidinyl]amino]carbonyl]amino]sulfonyl]benzoate; imazamethabenz (-methyl); imazamox; imazapic; imazapyr; imazaquin and salts such as the ammonium salts; imazethapyr; imazosulfuron; inabenfide; indanofan; indaziflam; iodosulfuron-methyl (-sodium); ioxynil; isocarbamid; isopropalin; isoproturon; isouron; isoxaben; isoxachlortole; isoxaflutole; isoxapyrifop; karbutilate; lactofen; lenacil; linuron; maleic hydrazide (MH); MBTA; MCPA; MCPB; mecoprop(-P); mefenacet; mefluidide; mepiquat(-chloride); mesosulfuron(-methyl); mesotrione; metam; metamifop; metamitron; metazachlor; methabenzthiazuron; metham; methazole; methoxyphenone; methylarsonic acid; methyl-cyclopropene; methyldymron; methylisothiocyanate; methabenzthiazuron; metobenzuron; metobromuron; (alpha-)metolachlor; metosulam (XRD 511); metoxuron; metribuzin; metsulfuron-methyl; molinate; monalide; monocarbamide dihydrogensulfate; monolinuron; monuron; monosulfuron; MT 128, i.e., 6-chloro-N-(3-chlor-2-propenyl)-5-methyl-N-phenyl-3-pyridazinamine; MT 5950, i.e., N-[3-chloro-4-(1-methylethyl)-phenyl]-2-methylpentanamide; naproanilide; napropamide; naptalam; NC 310, i.e., 4-(2,4-dichlorbenzoyl)-1-methyl-5-benzyloxypyrazole; neburon; nicosulfuron; nipyraclofen; nitralin; nitrofen; nitrophenolate mixture; nitrofluorfen; nonanoic acid; norflurazon; orbencarb; orthosulfamuron; oxabetrinil; oryzalin; oxadiargyl (RP-020630); oxadiazon; oxasulfuron; oxaziclomefone; oxyfluorfen; paclobutrazol; paraquat(-dichloride); pebulate; pelargonic acid; pendimethalin; penoxulam; pentachlorophenol; pentanochlor; pentoxazone; perfluidone; pethoxamid; phenisopham; phenmedipham; picloram; picolinafen; pinoxaden; piributicarb; pirifenop-butyl; pretilachlor; primisulfuron(-methyl); probenazole; procarbazone-(sodium); procyazine; prodiamine; profluralin; profoxydim; prohexadione(-calcium); prohydrojasmon; proglinazine(-ethyl); prometon; prometryn; propachlor; propanil; propaquizafop and its esters; propazine; propham; propisochlor; propoxycarbazone(-sodium) (MKH-6561); propyzamide; prosulfalin; prosulfocarb; prosulfuron (CGA-152005); prynachlor; pyraclonil; pyraflufen(-ethyl) (ET-751); pyrasulfotole; pyrazolynate; pyrazon; pyrazosulfuron(-ethyl); pyrazoxyfen; pyribambenz-isopropyl (ZJ 0702); pyrimbambenz-propyl (ZJ 0273); pyribenzoxim; pyributicarb; pyridafol; pyridate; pyriftalid; pyriminobac(-methyl) (KIN-6127); pyrimisulfan (KIN-5996); pyrithiobac(-sodium) (KIN-2031); pyroxasulfone (KIN-485); pyroxofop and its esters (e.g., propargyl ester); pyroxsulam; quinclorac; quinmerac; quinoclamine; quinofop and its ester derivatives, quizalofop and quizalofop-P and the ester derivatives thereof, e.g., quizalofop-ethyl; quizalofop-P-tefuryl and -ethyl; renriduron; rimsulfuron (DPX-E 9636); S 275, i.e., 2-[4-chloro-2-fluoro-5-(2-propynyloxy)-phenyl]-4,5,6,7-tetrahydro-2H-indazole; secbumeton; sethoxydim; siduron; simazine; simetryn; sintofen; SN 106279, i.e., 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate (ICI-A0224); sulfosulfuron; TCA(-sodium); tebutam (GCP-5544); tebuthiuron; tecnacene; tefuryltrione; tembotrione; tepraloxydim; terbacil; terbucarb; terbuchlor; terbumeton; terbuthylazine; terbutryn; TFH 450, i.e., N,N-diethyl-3-[(2-ethyl-6-methylphenyl)-sulfonyl]-1H-1,2,4-triazole-1-carboxamide; thenylchlor (NSK-850); thiafluamide, thiazafluoron; thiazopyr (Mon-13200); thidiazimin (SN-24085); thidiazuron; thiencarbazone(-methyl); thifensulfuron(-methyl); thiobencarb; Ti 35; tiocarbazil; topramezone; tralkoxydim; tri-allate; triasulfuron; triaziflam; triazofenamide; tribenuron(-methyl); triclopyr; tridiphane; trietazine; trifloxysulfuron(-sodium); trifluralin; triflusulfuron and esters (e.g., methyl ester, DPX-66037); trimeturon; trinexapac; tritosulfuron; tsitodef; uniconazole; vernolate; WL 110547, i.e., 5-phenoxy-1-[3-(trifluoromethyl)-phenyl]-1H-tetrazole; D-489; ET-751; KIH-218; KIH-485 (pyrosysulfone); KIH-509; KPP-300; LS 82-556; NC-324; NC-330; DPX-N8189; SC-0774; DOWCO-535; DK-8910; V-53482; PP-600; MBH-001; TH-547; SYN-523; IDH-100; SYP-249; HOK-201; IR-6396; MTB-951; NC-620;
methyl 4-amino-3-chloro-6-(4-chloro-2-fluoro-3-methoxyphenyl)pyridine-2-carboxylate [CAS RN 943831-98-9];
4-amino-3-chloro-6-(4-chloro-2-fluoro-3-methoxyphenyl) pyridine-2-carboxylic acid [CAS RN 943832-60-8];
an agrochemically compatible salt of the compound 2-iodo-N-[(4-methoxy-6-methyl-1,3,5-triazin-2-yl)carbonyl]benzenesulfonamide; and
an agrochemically compatible salt of the compounds of the formula (II):

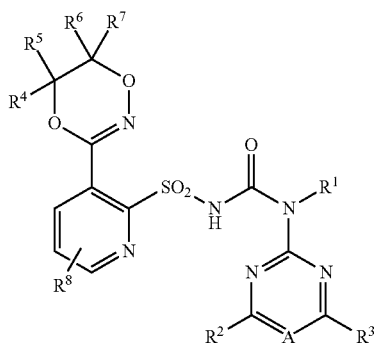

(II)

in which
A is nitrogen or a group $CR^{11}$,
where
$R^{11}$ is hydrogen, alkyl, halogen or haloalkyl,
$R^1$ is hydrogen or a radical which is optionally substituted in each case and is selected from the group consisting of alkyl, alkoxy, alkoxyalkyl, alkenyl, alkynyl, cycloalkyl, cycloalkylalkyl, aralkyl and aryl,
$R^2$ is hydrogen, halogen or an in each case optionally halogen-substituted alkyl, alkoxy, alkylthio, alkylamino or dialkylamino having in each case 1 to 6 carbon atoms,
$R^3$ is hydrogen, halogen or an in each case optionally halogen-substituted alkyl, alkoxy, alkylthio, alkylamino or dialkylamino having in each case 1 to 6 carbon atoms,
$R^4$-$R^7$ independently of one another are hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms, $R^8$ is hydrogen, halogen, cyano, thiocyanato or in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
where, in the radicals specified above, the alkyl and alkylene groups have in each case 1-6 carbon atoms, the alkenyl and alkynyl groups have in each case 2 to 6 carbon atoms, the cycloalkyl groups have in each case 3-6 carbon atoms, and the aryl groups have in each case 6 or 10.

If the respective common name encompasses two or more forms of the active compound, the common name preferably defines the form that is available commercially.

Particularly preferred further herbicides (C), which differ structurally from the herbicides (A) and (B), are amicarbazone, amidosulfuron; benzobicyclon; bicyclopyrone; bromoxynil; carfentrazone(-ethyl); chlorimuron(-ethyl); clefoxydim; clethodim; clomazone; clopyralid; cloransulam(-methyl); 2,4-D; desmedipham; dicamba; diflufenican; diflufenzopyr(-sodium); dimethenamid (SAN-582H); dimethenamid-P; ethoxysulfuron; fenoxaprop-P; fenoxaprop-P-ethyl; flucarbazone(-sodium); flufenacet; fluoroxypyr(-meptyl); foramsulfuron; imazamox; imazapic; imazapyr; imazaquin; imazethapyr; indaziflam; iodosulfuron-methyl(-sodium); ioxynil; isoproturon; isoxaben; isoxaflutole; lactofen; mefenacet; mesosulfuron(-methyl); mesotrione; metazachlor; metolachlor; metribuzin; metsulfuron-methyl; nicosulfuron; oxadiargyl (RP-020630); oxyfluorfen; pendimethalin; phenmedipham; picolinafen; pinoxaden; profoxydim; propanil; propoxycarbazone(-sodium) (MKH-6561); prosulfocarb; pyrazosulfuron(-ethyl); pyridate; pyroxsulam; rimsulfuron (DPX-E 9636); simazine; sulcotrione; sulfentrazone (FMC-97285, F-6285); sulfosate (ICI-A0224); tefuryltrione; tembotrione; thiencarbazone(-methyl); thifensulfuron(-methyl); topramezone; tribenuron(-methyl); triclopyr; trifloxysulfuron(-sodium); KIH-485 (pyrosysulfone); HOK-201 and methyl 4-amino-3-chloro-6-(4-chloro-2-fluoro-3-methoxyphenyl)pyridine-2-carboxylate [CAS RN 943831-98-9];
4-amino-3-chloro-6-(4-chloro-2-fluoro-3-methoxyphenyl) pyridine-2-carboxylic acid [CAS RN 943832-60-8];
an agrochemically compatible salt of the compound 2-iodo-N-[(4-methoxy-6-methyl-1,3,5-triazin-2-yl)carbonyl]benzenesulfonamide; and
an agrochemically compatible salt of the compounds of the formula (II).

Especially preferred further herbicides (C) which differ structurally from the herbicides (A) and (B) are amicarbazone (C1), amidosulfuron (C2), bicyclopyrone (C3), carfentrazone (C4), chlorimuron (C5), clefoxydim (C6), clethodim (C7), 2,4 D (C8), dicamba (C9), diflufenzopyr (C10), dimethenamid-P (DNTA-P) (C11), dimethenamid (C12), ethoxysulfuron (C13), fenoxaprop-P-ethyl (C14), flufenacet (C15), flucarbazone (C16), foramsulfuron (C17), imazamox (C18), imazapic (C19), imazaquin (C20), imazethapyr (C21), indaziflam (C22), iodosulfuron-methyl(-sodium) (C23), isoxaflutole (IFT) (C24), mesotrione (C25), metazachlor (C26), mesosulfuron (C27), nicosulfuron (C28), pendimethalin (C29), picolinafen (C30), profoxydim (C31), propoxycarbazone (C32), pyroxasulfone (C33), rimsulfuron (C34), sulfentrazone (C35), tembotrione (C36), thifensulfuron (C37), thiencarbazone (C38), topramezone (C39), tribenuron (C40), methyl 4-amino-3-chloro-6-(4-chloro-2-fluoro-3-methoxyphenyl)pyridine-2-carboxylate [CAS RN 943831-98-9] (C41);
4-amino-3-chloro-6-(4-chloro-2-fluoro-3-methoxyphenyl) pyridine-2-carboxylic acid [CAS RN 943832-60-8] (C42);

an agrochemically compatible salt of the compound 2-iodo-N-[(4-methoxy-6-methyl-1,3,5-triazin-2-yl)carbonyl]benzenesulfonamide (C43); and an agrochemically compatible salt of the compounds of the formula (II).

Each of the aforementioned further active compounds as per component (C) (i.e., active compounds (C1), (C2), (C*), etc.) may then be combined preferably with one of the dual combinations, in accordance with the scheme (A)+(B)+(C*) or else in accordance with the scheme (A)+(B)+(C1)+(C2), etc.

Dual combinations are herbicide combinations of one or more herbicides (A), i.e., (A1) and/or (A2), with one or more herbicides (B), i.e., (Ba) and/or (Bb). In particular, the dual combination of (A1b) and (Ba) and also the dual combination of (A2a) and (Ba).

Of particular interest is the application of the following triple combinations:

(A1b)+(Ba)+(C17), (A1b)+(Ba)+(C18), (A1b)+(Bb)+(C17), (A1b)+(Bb)+(C18), (A2a)+(Ba)+(C17), (A2a)+(Ba)+(C18), (A2a)+(Bb)+(C17), (A2a)+(Bb)+(C18), (A1b)+(Ba)+(C20), (A1b)+(Ba)+(C21), (A1b)+(Bb)+(C20), (A1b)+(Bb)+(C21), (A2a)+(Ba)+(C20), (A2a)+(Ba)+(C21), (A2a)+(Bb)+(C20), (A2a)+(Bb)+(C21), (A1b)+(Ba)+(C23), (A1b)+(Ba)+(C27), (A1b)+(Bb)+(C23), (A1b)+(Bb)+(C27), (A2a)+(Ba)+(C23), (A2a)+(Ba)+(C27), (A2a)+(Bb)+(C23), (A2a)+(Bb)+(C27), (A1b)+(Ba)+(C28), (A1b)+(Ba)+(C34), (A1b)+(Bb)+(C28), (A1b)+(Bb)+(C34), (A2b)+(Ba)+(C28), (A2b)+(Ba)+(C34), (A2b)+(Bb)+(C28), (A2b)+(Bb)+(C34).

Of very particular interest is the application of the following quadruple combinations:

(A1b)+(Ba)+(C17)+(C23), (A1b)+(Bb)+(C17)+(C23), (A2a)+(Ba)+(C17)+(C23), (A2a)+(Bb)+(C17)+(C23), (A1b)+(Ba)+(C27)+(C23), (A1b)+(Bb)+(C27)+(C23), (A2a)+(Ba)+(C27)+(C23), (A2a)+(Bb)+(C27)+(C23), (A1b)+(Ba)+(C18)+(C21), (A1b)+(Bb)+(C18)+(C21), (A2a)+(Ba)+(C18)+(C21), (A2a)+(Bb)+(C18)+(C21), (A1b)+(Ba)+(C18)+(C20), (A1b)+(Bb)+(C18)+(C20), (A2a)+(Ba)+(C18)+(C20), (A2a)+(Bb)+(C18)+(C20), (A1b)+(Ba)+(C28)+(C34), (A1b)+(Bb)+(C28)+(C34), (A2a)+(Ba)+(C28)+(C34), (A2a)+(Bb)+(C28)+(C34).

The weight ratio of the fraction composed of component (A) and component (B) in the herbicide combination to the fraction of component (C) is very preferably in the range between 1600:1:1600 to 1:10:0.05.

The weight ratio of the fraction composed of component (A) and component (B) in the herbicide combination to the fraction of component (C) is especially preferably in the range between 800:1:0.4 to 1:5:200.

The stated amounts are application rates (g of AC/ha=gram of active compound per hectare) and thus also define the ratios in a coformulation, a pre-mix, a tank mix or a sequential application of the combined active compounds.

The combinations can be applied both by the pre-emergence method and by the post-emergence method. This applies both to pre- and post-emergence with respect to the harmful plants and, in the selective control of harmful plants, to the pre- or post-emergence of the crop plants. Mixed forms are also possible, for example after the emergence of the crop plants the control of the harmful plants at their pre- or post-emergence stage.

Other suitable combination partners include crop plant-protecting active compounds (called "safeners" or "antidotes") which are able to prevent or reduce phytotoxic effects of the herbicides in crop plants.

Suitable safeners for the above-mentioned herbicidally active compounds (A) or combinations of herbicides (A) and (B) or generally for the combinations according to the invention are, for example, the following groups of compounds; the compounds are in each case referred to by the respective "common name" or code numbers with structure (references for the common names: see the "Pesticide Manual" mentioned above or "Compendium of Pesticide Common Names"):
benoxacor, cloquintocet(-mexyl), cyometrinil, cyprosulfamide, dichlormid, dicyclonon, dietholate, disulfoton (=O,O-diethyl S-2-ethylthioethyl phosphordithioate), fenchlorazole (-ethyl), fenclorim, flurazole, fluxofenim, furilazole, isoxadifen(-ethyl), mefenpyr(-diethyl), mephenate, naphthalic anhydride, oxabetrinil, "R-29148" (=3-dichloroacetyl-2,2,5-trimethyl-1,3-oxazolidine), "R-28725" (=3-dichloroacetyl-2,2,-dimethyl-1,3-oxazolidine), "PPG-1292" (=N-allyl-N-[(1,3-dioxolan-2-yl)methyl]-dichloroacetamide), "DKA-24" (=N-allyl-N-[(allylaminocarbonyl)methyl]-dichloroacetamide), "AD-67" or "MON 4660" (=3-dichloroacetyl-1-oxa-3-azaspiro[4,5]decane), "TI-35" (=1-dichloroacetylazepane), "dimepiperate" or "MY-93" (=5-1-methyl-1-phenylethyl piperidine-1-thiocarboxylate), "daimuron" or "SK 23" (=1-(1-methyl-1-phenylethyl)-3-p-tolylurea), "cumyluron"="JC-940" (=3-(2-chlorophenylmethyl)-1-(1-methyl-1-phenylethyl)urea), "methoxyphenone", or "NK 049" (=3,3'-dimethyl-4-methoxybenzophenone), "CSB" (=1-bromo-4-(chloromethylsulfonyl)benzene),
"CL-304415" (=4-carboxy-3,4-dihydro-2H-1-benzopyran-4-acetic acid; CAS-Regno: 31541-57-8), "MG-191" (=2-dichloromethyl-2-methyl-1,3-dioxolane), "MG-838" (=2-propenyl 1-oxa-4-azaspiro[4.5]decane-4-carbodithioate; CAS-Regno: 133993-74-5), methyl(diphenylmethoxy)acetate (CAS-Regno: 41858-19-9 from WO-A-1998/38856), methyl [(3-oxo-1H-2-benzothiopyran-4(3H)-ylidene)methoxy]acetate (CAS-Regno: 205121-04-6 from WO-A-1998/13361), 1,2-dihydro-4-hydroxy-1-methyl-3-(5-tetrazolylcarbonyl)-2-quinolone (CAS-Regno: 95855-00-8 from WO-A-1999/000020).

From among the safeners mentioned,
benoxacor, cloquintocet(-mexyl), cyometrinil, cyprosulfamide, dichlormid, fenchlorazole(-ethyl), fenclorim, flurazole, fluxofenim, furilazole, isoxadifen(-ethyl), mefenpyr(-diethyl), naphthalic anhydride, oxabetrinil, "AD-67" (="MON 4660"=3-dichloroacetyl-1-oxa-3-azaspiro[4,5]decane), "TI-35" (=1-dichloroacetylazepane), dimepiperate, daimuron, cumyluron, are of particular interest.

Some of the safeners have already been mentioned as herbicides and, accordingly, in addition to the herbicidal action on harmful plants, also have a protective action on the crop plants.

Each of the safeners mentioned can be combined as further active compound (C) preferably with one of the two-combinations mentioned which comprises a compound (B) having a structure different from the compound (C) in question, according to the scheme (A)+(B)+(C).

The herbicide combinations according to the invention may comprise further components, for example other active compounds against harmful organisms such as harmful plants, plant-damaging animals or plant-damaging fungi, in particular active compounds from the group consisting of fungicides, insecticides, acaricides, nematicides, miticides, and related substances.

Fungicidally active compounds which can be used in combination with the herbicide combinations according to the invention are preferably commercially available active compounds, for example (analogously to the herbicides, the compounds are generally referred to by their common names):
2-phenylphenol; 8-hydroxyquinoline sulfate; acibenzolar-5-methyl; actinovate; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; binapacryl; biphenyl; bitertanol; blasticidin-S; boscalid; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; cis-1-(4-chlorophenyl)-2-(1H-1,2,4-triazol-1-yl)cycloheptanol; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; methyl 1-(2,3-dihydro-2,2-dimethyl-1H-inden-1-yl)-1H-imidazole-5-carboxylate; methyl 2-[[[cyclopropyl[(4-methoxyphenyl)imino]methyl]thio]methyl]-.alpha.-(methoxymethylene)benzeneacetate; methyl 2-[2-[3-(4-chlorophenyl)-1-methyl-allylideneaminooxymethyl]phenyl]-3-methoxyacrylate; metiram; metominostrobin; metrafenone; metsulfovax; mildiomycin; monopotassium carbonate; myclobutanil; myclozolin; nabam, N-(3-ethyl-3,5,5-trimethylcyclohexyl)-3-formylamino-2-hydroxy-benzamide; N-(6-methoxy-3-pyridinyl)cyclopropanecarboxamide; N-butyl-8-(1,1-dimethylethyl)-1-oxaspiro[4.5]decan-3-amine; natamycin; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; penthiopyrad; phosdiphen; phthalide; picobenzamid; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; silthiofam; simeconazole; sodium tetrathiocarbonate; spiroxamine; sulfur; tebuconazole; tecloftalam; tecnazene; tetcyclacis; tetraconazole; thiabendazole; thicyofen; thifluzamide; thiophanate-methyl; thiram; tiadinil; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4- chlorophenyl)-2-propynyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)pyridine; 2,4-dihydro-5-methoxy-2-methyl-4-[[[[1-[[3-(trifluoro-methyl)phenyl]ethylidene]amino]oxy]methyl]phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; 3-[(3-bromo-6-fluoro-2-methyl-1H-indol-1-yl)sulfonyl]-N,N-dimethyl-1H-1,2,4-triazole-1-sulfonamide; copper salts and copper preparations, such as Bordeaux mixture; copper hydroxide; copper naphthenate; copper oxychloride; copper sulfate; cufraneb; copper(I) oxide; mancopper; oxine-copper.

Preferred fungicides are selected from the group consisting of benalaxyl, bitertanol, bromuconazole, captafol, carbendazim, carpropamid, cyazofamid, cyproconazole, diethofencarb, edifenphos, fenpropimorph, fentine, fluquinconazole, fosetyl, fluoroimide, folpet, iminoctadine, iprodionem, iprovalicarb, kasugamycin, maneb, nabam, pencycuron, prochloraz, propamocarb, propineb, pyrimethanil, spiroxamine, quintozene, tebuconazole, tolylfluanid, triadimefon, triadimenol, trifloxystrobin, zineb.

Insecticidal, acaricidal, nematicidal, miticidal and related active compounds are, for example (analogously to the herbicides and fungicides, the compounds are, if possible, referred to by their common names):
alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, trans-fluthrin, ZXI 8901, pyrethrins (pyrethrum), DDT, indoxacarb, acetamiprid, clothianidin, dinotefuran, imidacloprid, nitenpyram, nithiazine, thiacloprid, thiamethoxam, nicotine, bensultap, cartap, camphechlor, chlordane, endosulfan, gamma-HCH, HCH, heptachlor, lindane, methoxychlor spinosad, acetoprole, ethiprole, fipronil, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacryl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, Bacillus thuringiensis strains, spirodiclofen, spiromesifen, 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg. No.: 203313-25-1) (spirotetramat), flonicamid, amitraz, propargite, N2-[1,1-dimethyl-2-(methylsulfonyl)ethyl]-3-iodo-N1-[2-methyl-4-[1,2,2,2-tetrafluoro-1-(trifluoromethyl)ethyl]phenyl]-1,2-benzenedicarboxamide (CAS Reg. No.: 272451-65-7), thiocyclam hydrogen oxalate, thiosultap-sodium, azadirachtin, Bacillus spec., Beauveria spec., codlemone, Metarrhizium spec., Paecilomyces spec., thuringiensin, Verticillium spec., aluminum phosphide, methyl bromide, sulfuryl fluoride, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin.

Preferred insecticides which may be used together with the herbicides are selected from the group consisting of:
acetamiprid, acrinathrin, aldicarb, amitraz, acinphos-methyl, cyfluthrin, carbaryl, cypermethrin, deltamethrin, endosulfan, ethoprophos, fenamiphos, fenthion, fipronil, imidacloprid, methamidophos, methiocarb, niclosamide, oxydemeton-methyl, prothiophos, silafluofen, thiacloprid, thiodicarb, tralomethrin, triazophos, trichlorfon, triflumuron, terbufos, fonofos, phorate, chlorpyriphos, carbofuran, tefluthrin.

The active compound combinations according to the invention are suitable for controlling a broad spectrum of weeds on non-crop land, on paths, rail tracks, industrial terrain ("industrial weed control") or in plantation crops, such as moderate, subtropical and tropical climates or geographies. Examples of plantation crops are oil palms, nuts (for example almonds, hazelnuts, walnuts, macadamia), coconut, berries, oil palms, rubber tree, citrus (for example orange, lemon, mandarin), bananas, pineapples, cotton, sugarcane, tea, coffee, cacao and the like. They are also suitable for use in the cultivation of fruits (for example pome fruit, such as apple, pear, cherry, mango, kiwi) and viticulture.

The compositions can also be used in particular for preparing the soil for sowing ("burn-down" "no-till" or "zero-till" method or pre-emergence (direct seed)) or for treatment after harvest ("chemical fallow"). Potential applications of the active compound combinations extend to weed control in tree crops, for example young Christmas tree crops or eucalyptus plantations, in each case prior to planting or after transplanting (also by over-top treatment).

The compositions can also be used in selected crops of economically important crops, such as cereals (wheat, barley, rye, oats, sorghum, corn and rice), sugarbeet, sugarcane, oil seed rape, cotton, soybean, potatoes, tomatoes, peas and other varieties of vegetables. When using the active compounds (A) and (B) in crop plants such as cereals and corn, it may, depending on the crop plant, be expedient to apply a safener above certain application rates to prevent or reduce damage to the crop plant.

The herbicidally active compound combinations according to the invention in the respective use forms (=herbicidal compositions) are synergistically effective with respect to herbicide action and selectivity and have a favorable action with regard to the weed spectrum (including species having developed single or multiple (cross-)-resistances to various mechanisms of action such as ALS, EPSP, ACCase, etc.). They also have excellent herbicidal activity against a broad spectrum of economically important monocotyledonous or dicotyledonous annual harmful plants. The active compounds even act efficiently on perennial harmful plants which produce shoots from rhizomes, root stocks or other perennial organs and which are difficult to control.

For use, the active compound combinations can be applied to the plants (for example harmful plants, such as monocotyledonous or dicotyledonous weeds or unwanted crop plants), the seed (for example grains, seeds or vegetative propagation organs, such as tubers or shoot parts with buds) or to the area in which the plants grow (for example the area under cultivation).

In this context, the substances can be applied before sowing (if appropriate also by incorporation into the ground), pre-emergence or post-emergence. Application by the early post-sowing pre-emergence method or by the post-emergence method of plantation crops against harmful plants which have not yet emerged or which have already emerged is preferred. The application may also be integrated into weed management systems with repeat split applications (sequence applications, sequentials).

Specifically, examples may be mentioned of some representatives of the monocotyledonous and dicotyledonous weed flora which can be controlled by the active compound combinations according to the invention, without the enumeration being a restriction to certain species.

From among the monocotyledonous weed species, for example, the compositions control *Aegilops, Agropyron, Agrostis, Alopecurus, Apera, Avena, Brachicaria, Bromus, Cynodon, Dactyloctenium, Digitaria, Echinochloa, Eleocharis, Eleusine, Eragrostis, Eriochloa, Festuca, Fimbristylis, Imperata, Ischaemum, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum, Sphenoclea* and *Cyperus* species from the annual group.

In the case of dicotyledonous weed species, the activity spectrum extends to species such as, for example, *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erodium, Erysimum, Euphorbia, Galeopsis, Galinsoga, Galium, Geranium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the active compound combinations according to the invention are applied to the soil surface before germination, then the weed seedlings are either prevented completely from emerging, or the weeds grow until they have reached the cotyledonous stage but then their growth stops, and, eventually, after three to four weeks have elapsed, they die completely.

If the active compounds are applied post-emergence to the green parts of the plants, growth stops after the treatment and the harmful plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rain fastness of the active compounds in the combinations according to the invention is advantageous. A particular advantage is that the dosages of compounds (A) and (B), which are used in the combinations and are effective, can be adjusted to such a low quantity that their soil action is optimally low. Not only does this allow them to be employed in sensitive crops in the first place, but ground water contaminations are virtually avoided. The combination according to the invention of active compounds allows the application rate of the active compounds required to be reduced considerably.

The combined use of the herbicides (A) and (B) and, where used, (C) achieves application properties which exceed what would have been expected based on the known properties of the individual herbicides for their combination. For example, for a certain species of harmful plant, the herbicidal activities exceed the expected value estimated by standard methods, for example according to Colby (see below) or other extrapolation methods.

The synergistic effects therefore allow, for example, the application rates of the individual active compounds to be reduced, a higher efficacy at the same application rate, the control of previously uncontrolled species of harmful plants (gaps), higher residual action, longer long-term action, a more rapid onset of action, an extension of the period of application and/or a reduction of the number of individual applications required and—as a result for the user—weed control systems which are more advantageous economically and ecologically.

While the combinations according to the invention have an outstanding herbicidal activity against monocotyledonous and dicotyledonous weeds, many economically important crop plants are damaged only to a minor extent, if at all, depending on the structure of the respective active compound combinations according to the invention and their application rate. Economically important crops are in this context, for example, dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum* and *Zea.*

Some of the compositions according to the invention additionally have outstanding growth-regulatory properties in crop plants. They engage in a plant's metabolism in a regulatory fashion and can thus be employed for targeted influencing of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops, allowing lodging to be reduced or prevented completely.

On account of their herbicidal and plant growth-regulatory properties, the compositions can be employed for controlling harmful plants in crops of known plants or tolerant crop plants which are yet to be developed and are modified by conventional mutagenesis or genetically. As a rule, the transgenic plants are distinguished by particularly advantageous properties, in addition to resistances to the compositions according to the invention, for example by resistances to plant diseases or plant pathogens, such as certain insects or microorganisms such as fungi, bacteria or viruses. Other particular properties relate, for example, to the harvested material with respect to quantity, quality, storability, composition and specific constituents. Thus, transgenic plants with an increased starch content or in which the quality of the starch is altered, or those having a different fatty acid composition of the harvested material, are known. Further particular properties can be found in a tolerance or resistance to abiotic stress factors, for example, heat, cold, drought, salt and ultraviolet radiation.

Preferably, the active compound combinations according to the invention can be used as herbicides in crops of useful plants which are resistant to or have been made genetically resistant to the phytotoxic actions of the herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of
recombinant modifications of crop plants for the purpose of modifying the starch synthesized in the plants (for example WO 92/11376, WO 92/14827, WO 91/19806),
transgenic crop plants which are resistant to other herbicides, for example to sulfonylureas (EP-A-0257993, U.S. Pat. No. 5,013,659),
transgenic crop plants, with the capability of producing *Bacillus thuringiensis* toxins (Bt toxins) which make the plants resistant to certain pests (EP-A-0142924, EP-A-0193259),
transgenic crop plants having a modified fatty acid composition (WO 91/13972).
genetically modified crop plants having novel constituents or secondary compounds, for example novel phytoalexins providing increased resistance to disease (EPA 309862, EPA0464461)
genetically modified plants having reduced photorespiration, which provide higher yields and have higher stress tolerance (EPA 0305398)
transgenic crop plants producing pharmaceutically or diagnostically important proteins ("molecular pharming")
transgenic crop plants distinguished by higher yields or better quality
transgenic crop plants distinguished by a combination, for example of the novel properties mentioned above ("gene stacking").

Multiple transgenic crop plants may be tolerant, depending on requirements, to glufosinate, glyphosate and/or imidazolinones.

A large number of molecular-biological techniques with which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg or Christou, "Trends in Plant Science" 1 (1996) 423-431).

To carry out such recombinant manipulations, nucleic acid molecules which permit a mutagenesis or a sequence modification by recombination of DNA sequences can be introduced into plasmids. For example, it is possible with the aid of standard methods to carry out base exchanges, to remove subsequences or to add natural or synthetic sequences. Adapters or linkers may be added to the fragments in order to link the DNA fragments to each other, see, for example, Sambrook et al., 1989, Molecular Cloning, A Laboratory Manual, 2nd Ed., Cold Spring Harbor Laboratory Press, Cold Spring Harbor, N.Y.; or Winnacker "Gene and Klone" [Genes and Clones], VCH Weinheim 2nd Edition 1996.

For example, plant cells with a reduced activity of a gene product can successfully be generated by expressing at least one suitable antisense RNA, a sense RNA to achieve a cosuppression effect or by expressing at least one suitably constructed ribozyme which specifically cleaves transcripts of the abovementioned gene product.

To this end, it is possible to use firstly DNA molecules which encompass all of the coding sequence of a gene product including any flanking sequences which may be present and secondly DNA molecules which only encompass parts of the coding sequence, it being necessary for these parts to be of sufficient length to cause an antisense effect in the cells. Also possible is the use of DNA sequences which have a high degree of homology with the coding sequences of a gene product but are not entirely identical thereto.

When expressing nucleic acid molecules in plants, the protein synthesized may be localized in any compartment of the plant cell. However, to achieve localization in a particular compartment, it is possible for example to link the coding region with DNA sequences which guarantee localization in a certain compartment. Sequences of this type are known to the person skilled in the art, (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants can be plants of any desired plant species, i.e. both monocotyledonous and dicotyledonous plants. Transgenic plants are thus obtainable which have modified properties as a result of overexpression, suppression or inhibition of homologous (=natural) genes or gene sequences, or expression of heterologous (=foreign) genes or gene sequences.

The active compound combinations according to the invention may preferably be used in transgenic crops which are tolerant or have been made tolerant to the active compounds employed.

Preferably, the active compound combinations according to the invention can also be used in transgenic crops resistant to growth substances, such as, for example, dicamba and 2,4-D, or to herbicides inhibiting essential plant enzymes, for example acetyl-CoA carboxylases acetolactate synthases (ALS), EPSP synthases, glutamine synthases (GS) or hydroxyphenylpyruvate dioxygenases (HPPD), respectively, to herbicides from the group of the phenoxyphenoxyacetic acids (FOPs), sulfonylureas, the glyphosates, glufosinates or benzoylisoxazoles and analogous active compounds.

With particular preference the active compound combinations according to the invention can be used in transgenic crop plants which are resistant to a combination of glyphosates and glufosinates, glyphosates and sulfonylureas or imidazolinones. With very particular preference the compounds of the invention can be used in transgenic crop plants such as, for example, maize or soybeans with the trade name or designation Optimum™ GAT™ (glyphosate ALS tolerant).

Furthermore, and with particular preference, the compounds of the invention can be used in transgenic plants which are resistant to synthetic auxins (e.g., 2,4 D) with "HRAC mode of action Class O" and aryloxy-phenoxy propionates (fops) with "HRAC mode of action Class A" (e.g., DHT, Dow Agroscience Herbicide Tolerance Trait), and also a combination of this resistance with glyphosate resistance.

Particularly preferred, furthermore, is the use of the active compound combinations according to the invention in glyphosate- and dicamba-resistant crop plants. The invention accordingly also provides a method for controlling unwanted vegetation, if appropriate in crops of useful plants, preferably on non-crop land or in plantation crops, wherein one or more herbicides of type (A) are applied with one or more herbicides of type (B) to the harmful plants, to parts of plants or to plant seeds (seed) thereof or to the area under cultivation.

The invention also provides for the use of the new combinations of compounds (A)+(B) for controlling harmful plants, if appropriate in crops of useful plants, preferably on non-crop land and in plantation crops.

The active compound combinations according to the invention can not only be present as mixed formulations of the two components, if appropriate with further active compounds, additives and/or customary formulation auxiliaries, which are then applied in a customary manner diluted with water, or are produced as tank mixes by joint dilution of the separately formulated or partially separately formulated components with water.

The compounds (A) and (B) or their combinations can be formulated in various ways, depending on the prevailing biological and/or chemico-physical parameters. Examples of generally suitable formulations which are possible are: wettable powders (WP), water-soluble powders (SP), emulsifiable concentrates (EC), water-soluble concentrates, aqueous solutions (SL), emulsions (EW), such as oil-in-water and water-in-oil emulsions, sprayable solutions or emulsions, oil- or water-based dispersions, oil dispersions (OD), suspoemulsions, suspension concentrates (SC), oil-miscible solutions, capsule suspensions (CS), dusts (DP), seed-dressing products, granules for spreading and soil application, granules (GR) in the form of microgranules, wettable granules, coated granules and adsorption granules, water-dispersible granules (WG), water-soluble granules (SG), ULV formulations, microcapsules or waxes.

The invention therefore also provides herbicidal and plant growth-regulatory compositions which comprise the active compound combinations according to the invention.

The individual formulation types are known in principle and are described, for example, in Winnacker-Küchler, "Chemische Technologie", Volume 7, C. Hanser Verlag Munich, 4th Ed. 1986, van Valkenburg, "Pesticide Formulations", Marcel Dekker, N.Y., 1973; K. Martens, "Spray Drying Handbook", 3rd Ed. 1979, G. Goodwin Ltd. London.

The formulation assistants required, such as inert materials, surfactants, solvents and further additives, are likewise known and are described, for example, in: Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active compounds such as other herbicides, fungicides, insecticides or other pest control agents (for example, acaricides, nematicides, molluscicides, rodenticides, aphicides, avicides, larvicides, ovicides, bactericides, virucides, etc.), and with safeners, fertilizers and/or growth regulators, for example in the form of a readymix or a tank mix.

Wettable powders are preparations which are uniformly dispersible in water and which, in addition to the active compound, also contain ionic and/or nonionic surfactants (wetters, dispersants), for example polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate, in addition to a diluent or inert substance. For preparing the wettable powders, the herbicidally active compounds are finely ground, for example in conventional apparatus such as hammer mills, blower mills and airjet mills, and simultaneously or subsequently admixed with the formulation auxiliaries.

Emulsifiable concentrates are prepared by dissolving the active compound in an organic solvent, e.g. butanol, cyclohexanone, dimethylformamide, xylene or else higher-boiling aromatics or hydrocarbons or mixtures of the organic solvents with addition of one or more surfactants of ionic and/or nonionic type (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or such as, for example, polyoxyethylene sorbitan fatty acid esters.

Dusts are obtained by grinding the active compound with finely divided solid materials, for example talc, natural clays such as kaolin, bentonite and pyrophyllite, or diatomaceous earth.

Suspension concentrates can be water-based or oil-based. They can be prepared, for example, by wet grinding using conventional bead mills, if appropriate with the addition of surfactants, as already listed, for example, above for the other formulation types.

Emulsions, for example oil-in-water emulsions (EW), can be prepared, for example, with the aid of stirrers, colloid mills and/or static mixers using aqueous organic solvents and, if appropriate, surfactants, for example as already listed above for the other formulation types.

Granules can be prepared either by spraying the active compound onto adsorptive, granulated inert material or by applying active compound concentrates to the surface of carriers such as sand, kaolinites or granulated inert material with the aid of stickers, for example polyvinyl alcohol, sodium polyacrylate or else mineral oils. Suitable active compounds can also be granulated in the fashion which is conventional for the production of fertilizer granules, if desired as a mixture with fertilizers.

Water-dispersible granules are generally prepared by methods such as spray drying, fluidized-bed granulation, disk granulation, mixing with high-speed stirrers and extrusion without solid inert material.

As a rule, the agrochemical preparations comprise 0.1 to 99% by weight, in particular 0.2 to 95% by weight, of active compounds of types (A) and/or (B), the following concentrations being customary depending on the type of formulation. In wettable powders, the active compound concentration is, for example, approximately 10 to 95% by weight, the remainder to 100% by weight being composed of customary formulation constituents. In the case of emulsifiable concentrates, the active compound concentration can amount to approximately 1 to 90% by weight, preferably 5 to 80% by weight.

Formulations in the form of dusts comprise in most cases 5 to 20% by weight of active compound, and sprayable solutions comprise approximately 0.05 to 80, preferably 2 to 50, percent by weight (% by weight) of active compound.

In the case of granules such as dispersible granules, the active compound content depends partly on whether the active compound is in liquid or solid form and on the granulation auxiliaries and fillers which are being used. In the case of the water-dispersible granules, the active compound content is generally between 1 and 95% by weight, preferably between 10 and 80% by weight.

In addition, the active compound formulations mentioned comprise, if appropriate, respectively the conventional stickers, wetters, dispersants, emulsifiers, penetrants, preservatives, antifreeze agents, solvents, fillers, carriers, colorants, antifoams, evaporation inhibitors, and pH or viscosity regulators.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

The active compounds can be applied to the plants, parts of the plants, seeds of the plants or the area under cultivation (soil of a field), preferably to the green plants and parts of the plants and, if appropriate, additionally to the soil of the field. One possible use is the joint application of the active compounds in the form of tank mixes, the concentrated formulations of the individual active compounds, in optimal formulations, jointly being mixed with water in the tank and the resulting spray mixture being applied.

A joint herbicidal formulation of the combination according to the invention of active compounds (A) and (B) has the advantage of being easier to apply since the quantities of the components are already presented in the correct ratio to each other. Moreover, the assistants in the formulation can be matched optimally to each other, whereas a tank mix of different formulations may result in undesirable combinations of adjuvants.

A. General Formulation Examples a) A dust is obtained by mixing 10 parts by weight of an active compound (A) or (B) or of an active compound mixture (A)+(B) (and if appropriate further active compound components) and/or salts thereof and 90 parts by weight of talc as inert material and comminuting the mixture in a hammer mill.

b) A wettable powder which is readily dispersible in water is obtained by mixing 25 parts by weight of an active compound/active compound mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (® Triton X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of oxethylated nonylphenol as emulsifier.

e) Water-dispersible granules are obtained by mixing
75 parts by weight of an active compound/active compound mixture,
10 parts by weight of calcium lignosulfonate,
5 parts by weight of sodium lauryl sulfate,
3 parts by weight of polyvinyl alcohol and
7 parts by weight of kaolin,
grinding the mixture on a pinned-disk mill and granulating the powder in a fluidized bed by spraying on water as granulation liquid.

f) Water-dispersible granules are also obtained by homogenizing and precomminuting, in a colloid mill,
25 parts by weight of an active compound/active compound mixture,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

B. Biological Examples

1. Pre-Emergence Herbicidal Action

Seeds or rhizome pieces of monocotyledonous and dicotyledonous harmful plants are placed in sandy loam in pots and covered with soil. The compositions, formulated as concentrated aqueous solutions, wettable powders or emulsion concentrates, are then applied to the surface of the covering soil as an aqueous solution, suspension or emulsion at an application rate of 300 to 800 L of water/ha (converted) in a variety of dosages. After the treatment, the pots are placed in a greenhouse and kept under good growth conditions for the weeds. Visual scoring of plant or emergence damage is carried out after the test plants have emerged after an experimental period of 3 to 4 weeks in comparison with untreated controls. As demonstrated by the test results, the compositions according to the invention have a good pre-emergence herbicidal action against a broad spectrum of weed grasses and broad-leaf weeds.

Scoring and Assessing of the Synergistic Herbicidal Effects: The herbicidal efficacy of the active compounds or active compound mixtures was scored visually by comparing the treated pots (soil) with untreated controls. The damage and development of all above-ground plant parts was recorded. Scoring was done on a percentage scale (example values: 100% action=all plants dead or not emerged; 50% action=50% of the plants and green plant parts dead or not emerged; 0% action=no discernible action=like control plot). The score figures of in any case 2 repetitions (pots) were averaged.

When applying the combinations according to the invention, herbicidal effects are frequently observed on a harmful plant species which exceed the formal total of the effects of the herbicides present when these are applied by themselves. Alternatively, it is observed in some cases that a lower application rate is required for the herbicide combination in order to achieve the same effect on a harmful plant species in comparison with the individual products. Such increases in action or efficacy, or reduced application rates, strongly suggest a synergistic effect. When the data observed already exceed the formal total of the data in the experiments with individual applications, they likewise exceed the expected value according to Colby, which is calculated using the formula below and is likewise regarded as an indication of synergism (cf. S. R. Colby; in Weeds 15 (1967) pp. 20 to 22):

$$E = A + B - (A \cdot B/100)$$

In this formula:
A=action of active compound (A) in % at an application rate of a g of AS/ha;
B=action of active compound (B) in % at an application rate of b g of AS/ha;
E=expected value of the action of the combination (A)+(B) in % at the combined application rate a+b g of AS/ha.

The data observed in the experiments show, at suitably low dosages, an action of the combinations which exceeds the expected values according to Colby.

2. Post-Emergence Herbicidal Action

Seeds or rhizome pieces of monocotyledonous and dicotyledonous weeds are placed in sandy loam in pots, covered with soil and grown in the greenhouse under good growth conditions (temperature, atmospheric humidity, water supply). Three weeks after sowing, the test plants are treated in the three-leaf stage with the compositions according to the invention. The compositions according to the invention, formulated as wettable powders or emulsion concentrates, are sprayed onto the green plant parts in various dosages using an application rate of 300 to 800 L of water/ha (converted). After the test plants have remained in the greenhouse under optimum growth conditions for about 3 to 4 weeks, the effect of the preparations is scored visually in comparison with untreated controls (scoring as in Example 1). The compositions according to the invention also have good herbicidal post-emergence action against a broad spectrum of economically important weed grasses and broad-leaf weeds.

Here, effects of the combinations according to the invention are frequently observed which exceed the formal total of the effects of the herbicides when these are applied by themselves. The observed values for the tests show, at suitably low dosages, an effect of the combinations which exceeds the expected values according to Colby (cf. scoring in Example 1).

3. Pre- and Post-Emergence Herbicidal Action (Field Trials)

Corresponding to the greenhouse experiments of sections 1 and 2, the tests were carried out in the open on plots. Scoring was carried out analogously to the tests in sections 1 and 2.

4. Herbicidal Action and Crop Plant Tolerance (Field Trials)

Crop plants were grown in the open on plots under natural outdoor conditions, and seeds or rhizome pieces of typical harmful plants were laid out or the natural weed growth was utilized. Treatment with the compositions according to the invention was carried out after the harmful plants had emerged and the crop plants were, generally, at the 2- to 4-leaf stage; in some cases (as stated), application of individual active compounds or active compound combinations was carried out pre-emergence or as a sequential treatment partly pre-emergence and/or post-emergence.

In the case of plantation crops, it was generally only the soil between the individual crop plants that was treated with the active compounds.

After the application, for example 2, 4, 6 and 8 weeks after application, the effect of the preparations was scored visually by comparison with untreated controls (cf. scoring in Example 1). In the outdoor trial as well, the compositions according to the invention have synergistic herbicidal activity against a broad spectrum of economically important weed grasses and broad-leaf weeds. The comparison showed that the combinations according to the invention in most cases have a higher, in some cases a considerably higher, herbicidal activity than the total of the activities of the individual herbicides, thus indicating synergism. Moreover, the effects in essential phases of the scoring period were above the expected values according to Colby (cf. scoring in Example 1), also indicating synergism. In contrast, the crop plants were, as a consequence of the treatments with the herbicidal compositions, damaged only to a small degree, if at all.

5. Specific Test Examples

The following abbreviations are used in the description and the tables below:

g AS/ha=grams of active substance (=100% active compound) per hectare;

the total of the activities of the individual applications is given as $E^A$;

the expected values according to Colby would be named as $E^c$.

5.1 Examples

TABLE 1

Herbicidal action of saflufenacil (amorphous state) vs. saflufenacil (hydrate) - in combination with glufosinate-ammonium

| Active compound(s) | Dose G AS/ha | Herbicidal action [%] on *Digitaria sanguinalis* |
|---|---|---|
| Glufosinate-ammonium (A2a) | 450 | 15 |
| Compound of the formula (I) (amorphous) | 25 | 0 |
| Hydrate of the compound of the formula (I) = (Ba) | 25 | 0 |
| Glufosinate-ammonium (A2a) + compound of the formula (I) (amorphous) | 450 + 25 | 15 ($E^A$ = 15 + 0 = 15) |
| Glufosinate-ammonium (A2a) + hydrate of the compound of the formula (I) = (Ba) | 450 + 25 | 40 ($E^A$ = 15 + 0 = 15) |

The example summarized in table 1 shows that the combination of glufosinate and amorphous saflufenacil is merely additive in its action in controlling broad-leaf weeds.

In contrast, the herbicide combination comprising the hydrate of saflufenacil (Ba) and glufosinate each at the same dose exhibits a significantly synergistic effect. While the addition of the individual actions of the corresponding dose when applied for controlling *Digitaria sanguinalis* controls it to an extent of 15%, the combined application of glufosinate and a hydrate of saflufenacil (Ba) results in 40% successful control of the broad-leaf weed—in other words, in comparison to the addition of the individual action, the combination according to the invention produces a synergistic boost in action of 25%.

TABLE 2a

Herbicidal action of saflufenacil (amorphous state) vs. saflufenacil
(hydrate) - in combination with glyphosate isopropylammonium

| Active compound(s) | Dose g AS/ha | Herbicidal action [%] Cirsium Arvense |
|---|---|---|
| Glyphosate-isopropylammonium (A1b) | 675 | 25 |
| Compound of the formula (I) (amorphous) | 25 | 55 |
| Hydrate of the compound of the formula (I) = (Ba) | 25 | 45 |
| Glyphosate-isopropylammonium (A1b) + compound of the formula (I) (amorphous) | 675 + 25 | 85 ($E^A$ = 25 + 55 = 80) |
| Glyphosate-isopropylammonium (A1b) + hydrate of the compound of the formula (I) = (Ba) | 675 + 25 | 94 ($E^A$ = 25 + 45 = 70) |

Table 2a summarizes the herbicidal action of a combination comprising glyphosate-isopropylammonium (A1b) and a hydrate of saflufenacil (Ba). In application for controlling *Cirsium arvense*, the combination comprising glyphosate and the amorphous form of saflufenacil shows only weakly synergistic boost in action, of 5% in comparison to the addition of the individual actions for the corresponding dose.

In contrast, the composition comprising glyphosate and the hydrate of saflufenacil (Ba) shows a boost in action of 24% in comparison to the anticipated sum of the individual actions.

TABLE 2b

Herbicidal acition for controlling dicotyledonous weeds - saflufenacil
(hydrate) in combination with glyphosate-isopropylammonium

| Active compound(s) | Dose g AS/ha | Herbicidal action [%] Abutilon teophrastis | Herbicidal action [%] Euphorbia heterophylla | Herbicidal action [%] Xanthium strumarium |
|---|---|---|---|---|
| Glyphosate-isopropylammonium (A1b) | 100 | 10 | 10 | 10 |
| Hydrate of the compound of the formula (I) = (Ba) | 6.25 | 75 | 30 | 30 |
| (A1b) + (Ba) | 6.25 + 100 | 100 ($E^A$ = 10 + 75 = 85) | 98 ($E^A$ = 10 + 30 = 40) | 50 ($E^A$ = 10 + 30 = 40) |

Table 2b summarizes the herbicidal action of a combination comprising glyphosate-isopropylammonium (A1b) and a hydrate of saflufenacil (Ba) for controlling dicotyledonous weeds.

The application corresponds to the procedure disclosed in Paragraph B. Biological Examples, wherein the active compounds were applied at the 2-3 leaf stage and scoring was carried out 28 days after application.

The expected value, given as $E^A$ which is calculated by addition, in all three examples is lower than the scored value for herbicidal action.

The synergistic increase in herbicidal action for the combination comprising the active compounds (A1b) and (Ba) is highest in *Euphorbia heterophylla*.

TABLE 2c

Herbicidal acition for controlling monocotyledonous
weeds - saflufenacil (hydrate) in combination with
glyphosate-isopropylammonium

| Active compound(s) | Dosis g AS/ha | Herbicidal action [%] Setaria faberii | Herbicidal action [%] Setaria viridis |
|---|---|---|---|
| Glyphosate-isopropylammonium (A1b) | 100 | 10 | 20 |
| Hydrate of the compound of the formula (I) = (Ba) | 6.25 | 30 | 25 |
| (A1b) + (Ba) | 6.25 + 100 | 75 ($E^A$ = 10 + 30 = 40) | 100 ($E^A$ = 20 + 25 = 45) |

Table 2c summarizes the herbicidal action of a combination comprising glyphosate-isopropylammonium (A1b) and a hydrate of saflufenacil (Ba) for controlling monocotyledonous weeds.

The application corresponds to the procedure disclosed in Paragraph B. Biological Examples, wherein the active compounds were applied at the 1-2 leaf stage and scoring was carried out 28 days after application.

The expected value, given as $E^A$ which is calculated by addition, in all three examples is lower than the scored value for herbicidal action.

The synergistic increase in herbicidal action for the combination comprising the active compounds (A1b) and (Ba) is high for both examples.

TABLE 3

Herbicidal action of a combination comprising
3 active compounds

| Active compound(s) | Dose g AS/ha | Herbicidal action [%] Bidens pinata |
|---|---|---|
| Glyphosate-isopropylammonium (A1b) | 100 | 10 |
| Hydrate of the compound of the formula (I) = (Ba) | 6.25 | 40 |
| Glyphosate-isopropylammonium (A1b) + hydrate of the compound of the formula (I) = (Ba) | 100 + 6.25 | 85 ($E^A$ = 40 + 10 = 50) |
| Imazamox (C18) | 0.5 | 0 |

TABLE 3-continued

Herbicidal action of a combination comprising 3 active compounds

| Active compound(s) | Dose g AS/ha | Herbicidal action [%] Bidens pinata |
|---|---|---|
| Glyphosate-isopropylammonium (A1b) + hydrate of the compound of the formula (I) = (Ba) + imazamox (C18) | 100 + 6.25 + 0.5 | 99 ($E^A$ = 40 + 10 + 0 = 50) 0 |

Table 3 summarizes the herbicidal action of a combination of three active compounds, namely glyphosate-isopropylammonium (A1b), a hydrate of saflufenacil (Ba) and imazamox (C18). In application for controlling *Bidens pinata*, the combination comprising glyphosate and the amorphous form of saflufenacil shows a synergistic boost in action, of 35% in comparison to the addition of the individual actions for the corresponding dose, while the active compound imazamox (C18) alone shows no herbicidal action.

In contrast, the composition comprising glyphosate, a hydrate of saflufenacil (Ba) and imazamox (C18) as well shows a boost in action of 49% in comparison to the anticipated sum of the individual actions.

TABLE 4a

Dosage and weight ratio of components for the combinations (A) + (B)

| Active compounds | Dose | Weight ratio |
|---|---|---|
| (A) + (B) | 3200 - 50 g AS/ha (A) + 500 - 2 g AS/ha (B) | 1600:1 to 1:10 |
| (A) + (B) | 2400 - 80 g AS/ha (A) + 400 - 3 g AS/ha (B) | 800:1 to 1:5 |

Table 4a summarizes the preferred proportions of components for the combination (A)+(B) and the corresponding doses in g ai/ha.

TABLE 4b

Dosage and weight ratio of components for the combinations (A) + (B) + (C)

| Active compounds | Dose | Weight ratio |
|---|---|---|
| (A) + (B) + (C) | 3200 - 50 g AS/ha (A) + 500 - 2 g AS/ha (B) + 5000 - 2 g AS/ha (C) | 1600:1:1 to 1:10:100 |
| (A) + (B) + (C) | 2400 - 80 g AS/ha (A) + 400 - 3 g AS/ha (B) + 3200 - 3 g AS/ha (C) | 800:1:1 to 1:5:40 |

Table 4b summarizes the preferred proportions of components for the combination (A)+(B)+(C) and the corresponding doses in g ai/ha.

What is claimed is:

1. A synergistic herbicidal composition, comprising:
   a) at least one herbicide (A) selected from the group consisting of
      glyphosate (A1) and agrochemically compatible salts thereof, and
      glufosinate (A2) and agrochemically compatible salts thereof, and
   b) a herbicide (B) comprising a crystalline hydrate of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide
   wherein the weight ratio of component (A) to component (B) is from 675:25 to 100:6.25.

2. The synergistic herbicidal composition as claimed in claim 1, wherein component (B) comprises a hydrate comprising 0.8 to 1.2 mol of water per mole of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide.

3. The synergistic herbicidal composition as claimed in claim 2, wherein component (B) has a melting point in the range from 100 to 140° C.

4. The synergistic herbicidal composition as claimed in claim 3, wherein component (B) has a 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide content of at least 94% by weight, based on the total amount of organic constituents present in the hydrate.

5. The synergistic herbicidal composition as claimed in claim 4, wherein component (B) in an X-ray powder diffractogram at 25° C. with Cu-Kα radiation shows at least one reflection at the 2θ value 11.6±0.2°.

6. The synergistic herbicidal composition as claimed in claim 5, wherein component (B) in an X-ray powder diffractogram additionally shows at least three of the following reflections reported as 2θ values: 5.1±0.2°, 10.1±0.2°, 10.8±0.2°, 13.9±0.2°, 15.1±0.2°, 16.1±0.2°, 17.9±0.2°, 20.2±0.2°, 24.5±0.2°.

7. The synergistic herbicidal composition as claimed in claim 4, wherein component (B) in an X-ray powder diffractogram at 25° C. with Cu-Kα radiation shows at least one reflection at the 2θ value 12.1±0.2°.

8. The synergistic herbicidal composition as claimed in claim 7, wherein component (B) shows at least three of the following reflections reported as 2θ values: 5.2±0.2°, 10.2±0.2°, 10.9±0.2°, 14.0±0.2°, 14.6±0.2°, 15.3±0.2°, 19.2±0.2°, 19.9±0.2°, 20.5±0.2°, 24.7±0.2°, 26.7±0.2°, 27.8±0.2°.

9. A synergistic herbicidal composition defined as claimed in claim 1 which when applied, is capable of controlling unwanted vegetation.

10. A synergistic herbicidal composition as claimed in claim 9 which, when applied, is capable of selectively controlling harmful plants in plant crops or for nonselectively controlling harmful plants.

11. A synergistic herbicidal composition as claimed in claim 10 which, when applied, is capable of selectively or nonselectively controlling harmful plants pre-emergence or post-emergence in multiple transgenic or mutagenic crops.

12. The synergistic herbicidal composition of claim 11, wherein said crops comprise maize, soybeans, cotton, oilseed rape, rice, sugar beet and/or cereals.

13. A method for controlling unwanted vegetation, comprising:
   applying
   a) at least one herbicide (A) selected from the group consisting of
      glyphosate (A1) and agrochemically compatible salts thereof, and
      glufosinate (A2) and agrochemically compatible salts thereof, and
   b) a herbicide (B) comprising a crystalline hydrate of 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide, wherein the herbicides (A) and (B) are applied together or separately, to plants, seed and/or an area on which plants grow.

* * * * *